United States Patent
Itu et al.

(10) Patent No.: US 10,134,129 B2
(45) Date of Patent: Nov. 20, 2018

(54) METHOD AND SYSTEM FOR HEMODYNAMIC COMPUTATION IN CORONARY ARTERIES

(71) Applicant: Siemens Healthcare GmbH, Erlangen (DE)

(72) Inventors: Lucian Itu, Brasov (RO); Puneet Sharma, Monmouth Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 248 days.

(21) Appl. No.: 15/304,145

(22) PCT Filed: Apr. 9, 2015

(86) PCT No.: PCT/US2015/025059
§ 371 (c)(1),
(2) Date: Oct. 14, 2016

(87) PCT Pub. No.: WO2015/164086
PCT Pub. Date: Oct. 29, 2015

(65) Prior Publication Data
US 2017/0046834 A1 Feb. 16, 2017

Related U.S. Application Data

(60) Provisional application No. 61/982,378, filed on Apr. 22, 2014.

(51) Int. Cl.
G06K 9/00 (2006.01)
G06T 7/00 (2017.01)
(Continued)

(52) U.S. Cl.
CPC .......... *G06T 7/0012* (2013.01); *A61B 5/0263* (2013.01); *A61B 6/507* (2013.01);
(Continued)

(58) Field of Classification Search
CPC ........ G06T 7/0012; G06T 2207/30104; G06T 7/20; G06T 7/60; A61B 5/0263;
(Continued)

(56) References Cited

U.S. PATENT DOCUMENTS 8,249,815 B2   8/2012  Taylor
9,087,147 B1 * 7/2015  Fonte ................. A61B 5/7275
(Continued)

FOREIGN PATENT DOCUMENTS

| CN | 104523260 A | 4/2015 |
| CN | 105559810 A | 5/2016 |
| WO | WO2013138428 A1 | 9/2013 |

OTHER PUBLICATIONS

Office Action dated Jul. 4, 2018 in corresponding Chinese Patent Application No. 201580020974.9.
(Continued)

*Primary Examiner* — Amir Alavi

(57) ABSTRACT

A method and system for computing blood flow in coronary arteries from medical image data disclosed. Patient-specific anatomical measurements of a coronary artery tree are extracted from medical image data of a patient. A reference radius is estimated for each of a plurality of branches in the coronary artery tree from the patient-specific anatomical measurements of the coronary artery tree. A flow rate is calculated based on the reference radius for each of the plurality of branches of the coronary artery tree. A plurality of total flow rate estimates for the coronary artery tree are calculated. Each total flow rate estimate is calculated from the flow rates of branches of particular generation in the coronary artery tree. A total flow rate of the coronary artery tree is calculated based on the plurality of total flow rate estimates. The total flow rate of the coronary artery tree can (Continued)

be used to derive boundary conditions for simulating blood flow in the coronary artery tree.

47 Claims, 4 Drawing Sheets

(51) Int. Cl.
| | |
|---|---|
| *G16H 50/50* | (2018.01) |
| *A61B 5/026* | (2006.01) |
| *A61B 6/00* | (2006.01) |
| *A61B 8/06* | (2006.01) |
| *G06F 17/11* | (2006.01) |
| *G06T 7/20* | (2017.01) |
| *G06T 7/60* | (2017.01) |
| *G06F 19/00* | (2018.01) |
| *A61B 34/10* | (2016.01) |

(52) U.S. Cl.
CPC .............. *A61B 8/06* (2013.01); *G06F 17/11* (2013.01); *G06F 19/00* (2013.01); *G06T 7/20* (2013.01); *G06T 7/60* (2013.01); *G16H 50/50* (2018.01); *A61B 2034/105* (2016.02); *G06T 2207/30104* (2013.01)

(58) Field of Classification Search
CPC ..... A61B 6/507; A61B 8/06; A61B 2034/105; G06F 19/3437; G06F 17/11
See application file for complete search history.

(56) References Cited

U.S. PATENT DOCUMENTS

| | | | |
|---|---|---|---|
| 2006/0050941 | A1 | 3/2006 | Middleton et al. |
| 2012/0072190 | A1 | 3/2012 | Sharma et al. |
| 2013/0246034 | A1 | 9/2013 | Sharma et al. |
| 2013/0272596 | A1 | 10/2013 | Xu et al. |
| 2014/0044330 | A1 | 2/2014 | Klingenbeck |
| 2014/0058715 | A1 | 2/2014 | Sharma et al. |
| 2014/0073977 | A1 | 3/2014 | Grady et al. |
| 2014/0200867 | A1* | 7/2014 | Lavi .................. G06F 19/321 703/2 |
| 2015/0065846 | A1* | 3/2015 | Choi .................. A61B 5/02007 600/407 |
| 2015/0339847 | A1* | 11/2015 | Benishti .............. G16H 50/30 382/131 |
| 2015/0374243 | A1* | 12/2015 | Itu ..................... G16H 50/50 703/2 |
| 2016/0022371 | A1* | 1/2016 | Sauer ................. A61B 6/504 600/407 |
| 2016/0296286 | A1* | 10/2016 | Bai .................... G16H 50/50 |
| 2016/0364860 | A1* | 12/2016 | Taylor ............... A61B 5/02007 |
| 2017/0046834 | A1* | 2/2017 | Itu ..................... G06T 7/60 |

OTHER PUBLICATIONS

Hutchins, G. M., Miner, M. M., Boitnott, J. K., "Vessel Caliber and Branch-Angle of Human Coronary Artery Branch-Points", Circulation Research, vol. 38, pp. 572-576, 1976.
Kamiya, A., Togawa, T., "Adaptive Regulation of Wall Shear Stress to Flow Change in the Canine Carotid Artery", American Journal of Physiology, vol. 239, pp. 14-21, 1980.
Kassab, G., Fung, Y., "The Pattern of Coronary Arteriolar Bifurcations and the Uniform Shear Hypothesis", Annals of Biomechanical Engineering, vol. 23, pp. 13-20, 1995.
Murray, C. D., "The Physiological Principle of Minimum Work: I. The Vascular System and the Cost of Blood Volume", Proc. of the National Academy of Sciences of the USA, vol. 12, pp. 207-214, 1926.
Murray, C. D., "The Physiological Principle of Minimum Work: II. Oxygen Exchange in Capillaries", Proc. of the National Academy of Sciences of the USA, vol. 12, pp. 299-304, 1926.
Uylings, H., "Optimization of Diameters and Bifurcation Angles in Lung and Vascular Tree Structures", Bulletin of Mathematical Biology, vol. 39, pp. 509-520, 1977.
van der Giessen, et al., "The Influence of Boundary Conditions on Wall Shear Stress Distribution in Patients Specific Coronary Trees", Journal of Biomechanics, vol. 44, pp. 1089-1095, 2011.
Zamir, M., Sinclair, P., Wonnacott, T. H., "Relation between Diameter and Flow in Major Branches of the Arch of the Aorta", Journal of Biomechanics, vol. 25, pp. 1303-1310, 1992.
PCT International Search Report and Written Opinion dated Jul. 6, 2015.

* cited by examiner

200

210

220

230

METHOD AND SYSTEM FOR HEMODYNAMIC COMPUTATION IN CORONARY ARTERIES

This application claims the benefit of U.S. Provisional Application No. 61/982,378, filed Apr. 22, 2014, the disclosure of which is herein incorporated by reference.

BACKGROUND OF THE INVENTION

The present invention relates to hemodynamic computation in coronary arteries based on medical image data, and more particularly, to simulating blood flow in coronary arteries based on medical image data for non-invasive functional assessment of coronary artery stenosis.

Cardiovascular disease (CVD) is the leading cause of deaths worldwide. Among various CVDs, coronary artery disease (CAD) accounts for nearly fifty percent of those deaths. Despite significant improvements in medical imaging and other diagnostic modalities, the increase in premature morbidity and mortality for CAD patients is still very high. The current clinical practice for diagnosis and management of coronary stenosis involves the assessment of the diseased vessel either visually or by Quantitative Coronary Angiography (QCA). Such assessment provides the clinician with an anatomical overview of the stenosis segment and parent vessel, including the area reduction, lesion length, and minimal lumen diameter, but does not provide a functional assessment of the effect of the lesion on blood flow through the vessel. Measuring the fractional flow reserve (FFR) by inserting a pressure wire into the stenosed vessel has been shown to be a better option for guiding revascularization decisions, since the FFR is more effective in identifying ischemia causing lesions, as compared to invasive angiography. QCA only evaluates the morphological significance of the stenosis and has a number of other limitations. Pressure wire based FFR measurements involve risks associated with the intervention necessary to insert the pressure wire into the vessel, and for a very narrow stenosis, the pressure wire may induce an additional pressure drop.

BRIEF SUMMARY OF THE INVENTION

The present invention provides a method and system for computing blood flow in coronary arteries from medical image data. Embodiments of the present invention utilize anatomical measurements of the coronary arteries in medical image data to estimate a resting blood flow rate in a patient-specific manner. Embodiments of the present invention use the estimated resting blood flow rate of the patient to perform blood flow simulations and compute derived hemodynamic metrics in the coronary arteries.

In one embodiment of the present invention, patient-specific anatomical measurements of a coronary artery tree are extracted from medical image data of a patient. A reference radius is estimated for each of a plurality of branches in the coronary artery tree from the patient-specific anatomical measurements of the coronary artery tree. A flow rate is calculated based on the reference radius for each of the plurality of branches of the coronary artery tree. A plurality of total flow rate estimates for the coronary artery tree are calculated, wherein each of the plurality of total flow rate estimates is calculated from the flow rates of branches from a respective one of a plurality of generations of branches. A total flow rate of the coronary artery tree is calculated based on the plurality of total flow rate estimates.

These and other advantages of the invention will be apparent to those of ordinary skill in the art by reference to the following detailed description and the accompanying drawings.

DETAILED DESCRIPTION

The present invention relates to a method and system for computing blood flow in coronary arteries from medical image data. Embodiments of the present invention are described herein to give a visual understanding of the method for computing blood flow in coronary arteries. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Computational fluid dynamics (CFD) based blood flow simulations can be used to estimate hemodynamic metrics, such as fractional flow reserve (FFR), for non-invasive functional assessment of stenosis severity in the coronary arteries. Such blood flow simulations typically require some information about the mass of volume of myocardium supplied by each coronary artery to provide an initial estimate of the blood flow in each coronary artery. Embodiments of the present invention do not rely on such characteristics of the myocardium. Embodiments of the present invention utilize only anatomical measurements of the coronary arteries in medical image data to estimate a patient-specific flow resting blood flow rate in the coronary arteries. Additionally, embodiments of the present invention can be applied separately in the left coronary tree and the right coronary tree, thereby obviating the need preparing a comprehensive coronary artery tree model, as in other methods.

Figure 1:
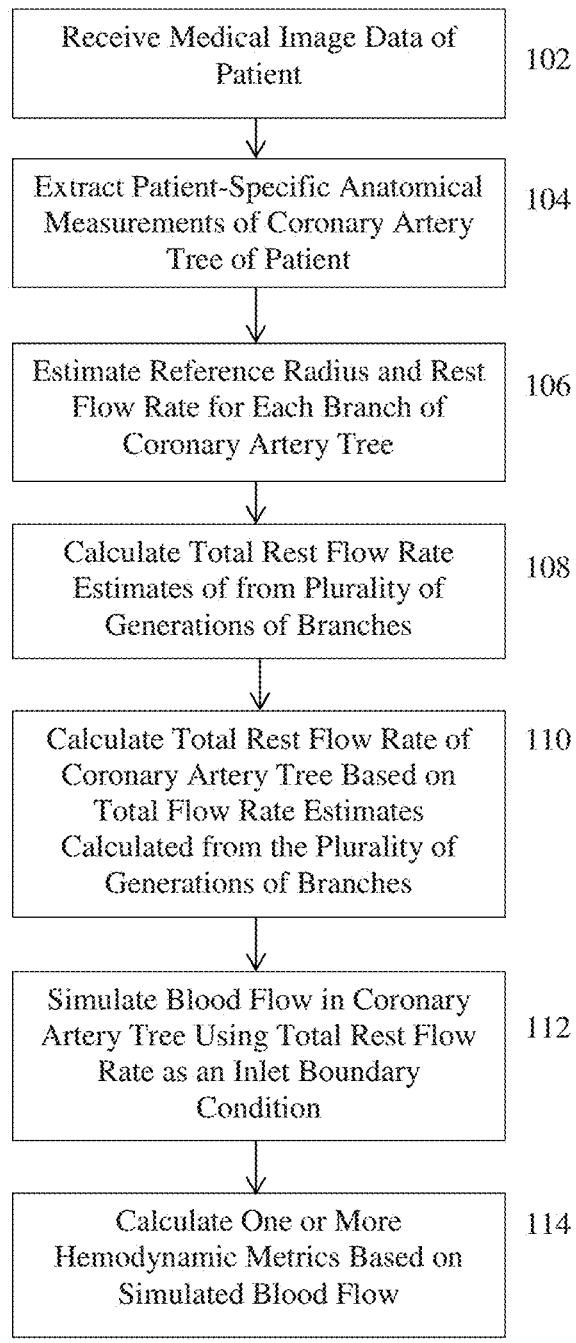
FIG. 1 illustrates a method of computing blood flow in coronary arteries from medical image data according to an embodiment of the present invention.

FIG. 1 illustrates a method for computing blood flow in coronary arteries from medical image data according to an embodiment of the present invention. The method of FIG. 1 transforms medical image data representing of patient's coronary region to generate a patient-specific anatomical model of the patient's coronary arteries and simulate blood flow in the patient's coronary arteries. At step 102, medical image data of a patient is received. Medical image data from one or multiple imaging modalities can be received. For example, the medical image data can include, computed tomography (CT), Dyna CT, magnetic resonance (MR), Angiography, Ultrasound, Single Photon Emission computed Tomography (SPECT), and any other type of medical imaging modality. The medical image data can be 2D, 3D, or 4D (3D+time) medical image data. The medical image data can be received directly from one or more image acquisition devices, such as a CT scanner, MR scanner, Angiography scanner, Ultrasound device, etc., or the medical image data may be received by loading previously stored medical image data for a patient.

In an advantageous embodiment, 3D coronary CT angiography (CTA) images are acquired on a CT scanner. The CTA images ensure that the coronary vasculature, including the vessel(s) that contain the stenosis, is adequately imaged using a contrast agent that is injected into the patient. At this stage, the clinician may be provided with an option of identifying lesions (stenoses) of interest by interactively viewing them on the images. This step can also be performed on a patient-specific anatomical model that is extracted from the image data (step 104). Alternatively, the stenoses may be automatically detected in the image data using an algorithm for automatic detection of coronary artery stenosis, such as the method for automatic detection of coronary artery stenosis described in U.S. Published Patent Application No. 2011/0224542, which is incorporated herein by reference. In addition to the medical image data, other non-invasive clinical measurements, such as the patient's heart rate and systolic and diastolic blood pressure may also be acquired.

At step 104, patient-specific anatomical measurements of a coronary artery tree are extracted from the medical image data. In an exemplary embodiment, the medical image data is acquired at rest-state and the measurements of the coronary arteries are extracted from the image data acquired at rest-state. The patient-specific anatomical measurements of the coronary artery tree can be patient-specific anatomical measurements for a full coronary artery tree of the patient or patient-specific anatomical measurements for any portion less than the full coronary artery tree of the patient. In a possible implementation, the patient-specific anatomical measurements of the coronary artery tree can be patient-specific anatomical measurements of only a left coronary artery (LCA) tree or a right coronary artery (RCA) tree. In an advantageous embodiment, the measurements of the coronary arteries are extracted by generating a patient-specific anatomical model of the coronary artery tree is generated from the medical image data, but the present invention is not limited thereto. The patient-specific anatomical model may be a patient-specific anatomical model of any portion of the full coronary artery tree of the patient. In order to generate the patient-specific anatomical model of the coronary artery tree, the coronary arteries can be segmented in the 3D medical image data using an automated coronary artery centerline extraction algorithm. For example, the coronary arteries can be segmented in a CT volume using the method described U.S. Published Patent Application No. 2010/0067760, which is incorporated herein by reference. Once a coronary artery centerline tree is extracted, cross-section contours can be generated at each point of the centerline tree. The cross-section contour at each centerline point gives a corresponding cross-section area measurement at that point in the coronary artery. A geometric surface model is then generated for the segmented coronary arteries. For example, methods for anatomical modeling of the coronary arteries are described in U.S. Pat. No. 7,860,290 and U.S. Pat. No. 7,953,266, both of which are incorporated herein by reference. In addition to the coronaries, the patient-specific anatomical model can include the aortic root together with the proximal part of the aorta. A detailed 3D model of each stenosis is also extracted using similar algorithms, which includes the quantification of the proximal vessel diameter and area, distal vessel diameter and area, minimal lumen diameter and area, and length of stenosis.

Figure 2:
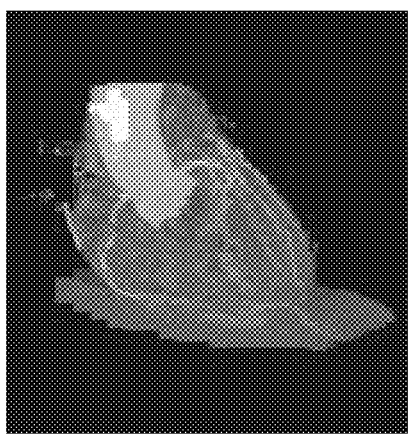
FIG. 2 illustrates exemplary results for generating a patient-specific anatomical model of the coronary vessel tree.
Figure 2:
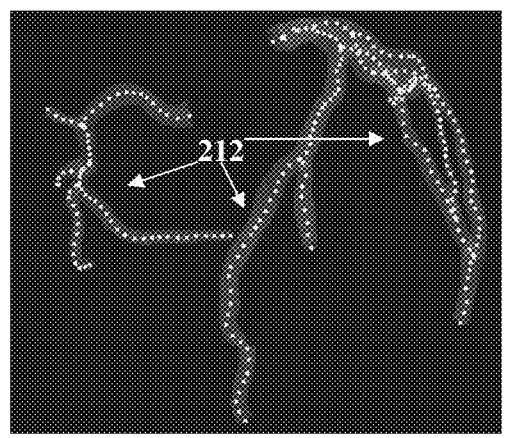
Figure 2:
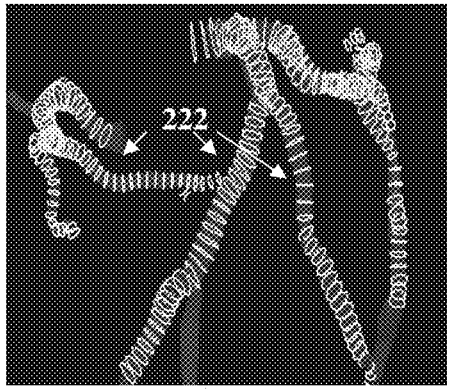
Figure 2:
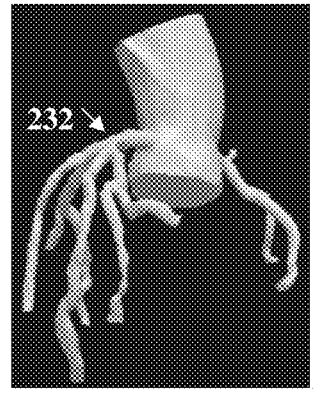

FIG. 2 illustrates exemplary results for generating a patient-specific anatomical model of the coronary vessel tree. Image 200 of FIG. 2 shows coronary CTA data. Image 210 shows a centerline tree 212 extracted from the CTA data. Image 220 shows a cross-section contours 222 extracted at each point of the centerline tree 212. Image 230 shows a 2D surface mesh 232 of the coronary arteries, the aortic root, and the proximal part of the aorta. It is to be understood that the anatomical model of the coronary tree of the patient can be output and displayed, for example on a display screen of the computer system.

Returning to FIG. 1, at step 106, a reference radius and rest flow rate is estimated for each branch of the coronary artery tree based on the patient-specific anatomical measurements. In particular, the reference radius is estimated for each branch based on the patient-specific anatomical measurements for that branch and the rest flow rate for each branch is calculated based on the reference radius for that branch. The following power law relationship has been established between flow rate and vessel reference radius in arterial circulation, and in particular for coronary circulation:

$$q = k \cdot r_{ref}^n,$$

where q is the average flow rate in the vessel, $r_{ref}$ is the reference radius of the vessel, k is a proportionality constant, and n is the power coefficient, which takes values between 2 (for large arteries) and 3 (for small arteries). Accordingly, the blood flow rate in a particular coronary artery branch can be expressed as a function of the reference radius and the power coefficient for that branch:

$$q = f_1(r_{ref}, n).$$

The value of the power coefficient k may be set from literature data, so as to obtain typical rest state flow rate values. Alternatively, the value of k may be set by matching invasive measurements with computed values in a large patient database. In this case, the computed values for the patients may refer directly to the flow rate, or to other quantities like velocity, or hemodynamic indices (FFR, CFR, iFR, etc.). It is possible that the same power coefficient value may be used for all patients. However, it is also possible that different power coefficient values may be set for different patients, based on patient characteristics, such as age, gender, etc. Different power coefficient values may also be set for different vessels (LAD, LCX, RCA, side branches, etc.). In a possible embodiment, the value of k may be adjusted account for the condition of increased coronary flow, for example when a patient is at a hyperemic state. In this case, the value of k is increased from the values used to estimate the rest flow rate such that the estimated flow rate corresponds to the blood flow at the hyperemic state of the patient.

For a patient-specific geometry, the radius of a branch is continuously changing along its centerline. Furthermore, the branch may contain mild to severe stenosis, which in turn can be focal, diffuse, etc. Thus, according to an advantageous embodiment, to compute the reference radius of a branch, an operator is applied to the longitudinally varying radius:

$$r_{ref} = f_2(r(x)),$$

where $f_2$ is the operator, r is the radius of the branch, and x is a position along a centerline of the branch. In a possible implementation, the operator $f_2$ can calculate an average value of healthy radiuses along the entire length of the branch or a part of the branch. When used herein, "healthy radiuses" refer to radiuses of healthy (non-stenosis) portions of a branch. As described above, stenosis regions can be automatically detected or manually identified and labeled on the patient-specific anatomical model of the coronary artery tree. Accordingly, the healthy portions of each branch can be automatically identified from the patient-specific anatomical model of the coronary artery tree. In another possible implementation, the operator $f_2$ can calculate an average value of the healthy radiuses along the entire length of the branch or a part of the branch, excluding the largest x % and the smallest y % of the healthy radius values. In another possible implementation, the operator $f_2$ can calculate the maximum or minimum value of healthy radiuses along the entire length of the branch or a part of the branch. It is to be understood that the operator $f_2$ is not necessarily limited to these operations and other possible calculations can also be used to estimate the reference radius of a branch.

In a patient-specific geometry, if a branch is very short (e.g., the length of the branch is less than a threshold) or branch displays diffuse disease along its entire length (e.g., a percentage of the branch that is diseased is greater than a threshold), the reference radius for that branch can be calculated as a function of the reference radius values of the parent, sibling, and/or daughter branches:

$$r_{ref} = f_3(r_{ref}^p, r_{ref}^s, r_{ref}^{d1}, r_{ref}^{d2}, \dots),$$

where $r_{ref}^p$ is the reference radius value for the parent branch from which the branch slits in the coronary artery tree, $r_{ref}^s$ is the reference radius value for a sibling branch (i.e., another branch that splits from the same parent branch), and $r_{ref}^{d1}$ and $r_{ref}^{d2}$ are reference radius values for daughter branches which split from the branch in the coronary artery tree. For example, the reference radius of a branch may be determined based on the reference radius values of the parent, sibling, and daughter branches as:

$$r_{ref} = \sqrt[n]{(r_{ref}^p)^n - (r_{ref}^s)^n} ; \text{ or } r_{ref} = \sqrt[n]{(r_{ref}^{d1})^n + (r_{ref}^{d2})^n}.$$

Once the reference radius values are estimated for each branch in the coronary artery tree, a rest flow rate is calculated based on the reference radius value for each branch in the coronary artery tree using the power law relationship described above. The rest flow rate calculated for each branch based on the reference radius is an estimate of the average flow rate or bulk flow rate for the blood flow in that branch.

Figure 3:
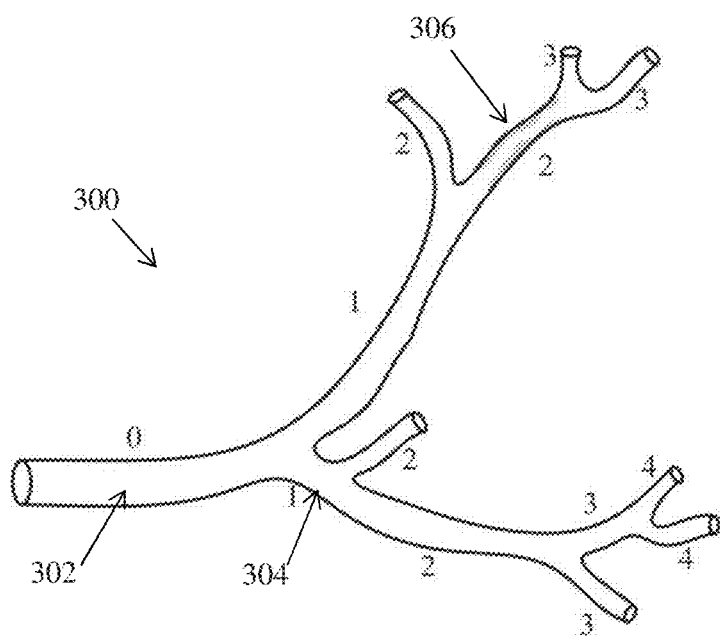
FIG. 3 illustrates an example of a coronary artery tree with a generation number assigned to each branch.

At step 108, total rest flow rate estimates are calculated from a plurality of generations of branches. FIG. 3 illustrates an example of a coronary artery tree 300 with a generation number assigned to each branch. As shown in FIG. 3, the root branch 302 of the coronary artery tree 300 has a generation number 0, and at each bifurcation the generation number increases by one. A separate estimate for the total flow rate of the coronary artery tree can be estimated from branches of each generation number. The total flow rate estimate for the coronary tree calculated using the branches with the generation number g is calculated as follows. Before estimating the total flow, a weight $w_i$ is assigned to each branch representing a confidence value for the correctness of the estimated reference radius for that branch. The branches can be weighted based on the length of the branch and/or the percentage of the branch that is diseased. Accordingly, short branches, such as the bottom branch 304 with the generation number equal to 1 in FIG. 3, or entirely diseased branches, such as the diffusely diseased branch 306 with the generation number equal to 2 in FIG. 3, are assigned low confidence values, while long branches without radius irregularities are assigned large confidence values. The weights (confidence values) may be normalized to range between 0 (minimum confidence) and 1 (maximum confidence). The weights can also be derived from the characteristics observed in the medical image, such as image quality, level of calcification, etc. For example a branch with relatively high calcification may be assigned a low confidence, while a branch with low or zero calcification may be assigned a very high confidence value. If there are artifacts (e.g., motion artifacts, metal artifacts, beam hardening artifacts, etc.) in a part of the image that was used to reconstruct a branch, the weight can also be a function of the local image quality of that region of interest. A total flow rate estimate for the entire coronary artery tree is then estimated based on the branches from generation g using the flow rates calculated for the branches and the weights assigned to the branches:

$$(q_{total})_g = f_4(w_i, q_i)$$

where the index i refers to all branches from generation g and all terminal branches with a generation number smaller than g. Terminal branches are branches that do not have any daughter branches (i.e., do not have any bifurcations into further branches with a higher generation number). In an exemplary implementation, the total flow rate estimate based on the branches from generation g can be calculated as:

$$(q_{total})_g = \frac{\Sigma_i w_i \cdot q_i}{\Sigma_i w_i}.$$

A plurality of total flow rate estimates are calculated by calculating respective a total flow rate estimate based on branches from each generation g between $g_{min}$ and $g_{max}$. In an advantageous implementation, the minimum generation level $g_{min}$ can be 0, but can also be larger than 0 if the root node is very short. The maximum generation level can be set to determine how many generations are used in calculating the total rest flow rate of the coronary artery tree. In advantageous implementations, the value for the maximum generation level $g_{max}$ may be set to 3 or 4. Branches of higher generations become increasingly smaller, which makes an accurate estimation of the reference radius and corresponding flow rate using the higher generation branches more difficult. Furthermore, when the anatomical model is reconstructed from medical images, small side branches may not be accounted for in the model. Hence, the higher the generation number, the higher the number of side branches not been considered will be, leading to a larger error in the flow rate estimation.

Returning to FIG. 1, at step 110, a total rest flow rate of the coronary artery tree is calculated based on the total flow rate estimates calculated from the plurality of generations of branches. To improve accuracy of the total flow rate estimation for the coronary artery tree, the flow rate estimates calculated from multiple different branch generations are used to calculate a final total flow rate value. In particular, the total flow rate estimates calculated from each generation g between $g_{min}$ and $g_{max}$ are used to calculate the final total flow rate value for the coronary artery tree. As described above, the minimum generation level $g_{min}$ can be 0, but can also be larger than 0 if the root node is very short, and the maximum generation level can be set to determine how many generations to use in calculating the total rest flow rate of the coronary artery tree. Before estimating the total flow rate for the coronary artery tree, a weight $v_i$ is assigned to each generation number, representing a confidence value for the correctness of the total flow rate estimate calculated from the branches with the corresponding generation number. For the patient-specific anatomical model of the coronary artery tree, low generation numbers can be assigned large weights, while large generation numbers can be assigned low weights as smaller side branches may be missed as the generation number increases, which may lead to an underestimation of the flow rate values. For example, the weights can have an inverse relationship to the generation number. The weights (confidence values) may be normalized to range between 0 (minimum confidence) and 1 (maximum confidence). The final total flow rate value is estimated as a function of the total flow rate estimates for the various generations and the corresponding weights assigned to the generations:

$$q_{total} = f_5(v_j, (q_{total})_j),$$

where the index j refers to a generation between $g_{min}$ and $g_{max}$. In an exemplary implementation, the total flow rate for the coronary artery tree can be calculated as:

$$q_{total} = \frac{\Sigma_j v_j \cdot (q_{total})_j}{\Sigma_j v_j}.$$

At step 112, blood flow in the coronary artery tree is simulated using the total rest flow rate as an inlet boundary condition. In an advantageous implementation, one or more computational fluid dynamics (CFD) simulations are used to simulate the blood flow in the coronary artery tree. The total rest flow rate calculated for the coronary artery tree is used as a patient-specific inlet boundary condition for the CFD simulation. In the CFD simulation, blood is modeled as a Newtonian fluid, and the velocity field is obtained by numerically solving the discretized Navier-Stokes equations (continuity and momentum equations) under the rigid wall assumption. The discretized Navier-Stokes equations are used to incrementally simulate velocity of blood flow and pressure within the coronary arteries over time. The patient-specific anatomy of the coronary arteries are also input to the CFD modeling in order to constrain the blood flow simulations based on the patient-specific anatomy. The CFD simulation results in simulated values for pressure and velocity of blood flow through the coronary arteries over time.

At step 114, one or more hemodynamic metrics are calculated based on the simulated blood flow in the coronary artery tree. For example, the patient-specific hemodynamic parameters can be calculated based on the CFD blood flow simulations. The CFD simulations result in simulated values for pressure and velocity of blood flow through the coronary arteries over time. These simulated values can be used to calculate various hemodynamic parameters, which can be used to assess coronary artery disease. For example, flow rates and pressure drops can be used for assessing the severity of the stenosis, and wall-shear stress can be used for assessing plaque formations. Hemodynamic metrics such as fractional flow reserve (FFR), rest Pd/Pa, instantaneous wave-free ratio (iFR), etc., can be calculated for a particular stenosis from the simulated flow rates and pressure in the coronary arteries. For example, rest Pd/Pa refers to a pressure drop over a stenosis (ratio of pressure distal to the stenosis (Pd) and aortal pressure (Pa)) at a rest state and can be calculated directly from the simulated pressures in the CFD simulation using the total rest flow rate as an inlet boundary condition. iFR refers to the ratio of Pd/Pa during a wave-free period in diastole and can also be calculated at the rest state from the simulated pressures in the CFD simulation using the total rest flow rate as an inlet boundary condition.

FFR is defined as the ratio of the maximal blood flow in the stenotic vessel to the maximal blood flow in a normal vessel, and is used to characterize the severity of stenosis. FFR can be approximated for a stenosis in the coronary artery tree by simulating the flow and pressure in the patient-specific anatomy of the coronary artery tree under a simulated hyperemic state, and calculating the ratio of the time-averaged pressure distal to the stenosis (Pd) with respect to the average pressure in the aorta (Pa) at the hyperemic state. In one possible embodiment, in order to simulate the blood flow and pressure at hyperemia, step 106 can be performed using a different operator $f_1$ to calculate the flow rate of each from the reference radius, such that a hyperemia flow rate is estimated for each branch instead of a rest flow rate. Steps 108 and 110 are performed as described above, but in this case result in a total hyperemia flow rate being calculated for the coronary artery tree, and in step 112, the blood flow simulation is performed using the total hyperemia flow rate as an inlet boundary condition, resulting in a simulation of hyperemic blood flow and pressure in the coronary artery tree. In another possible embodiment, total rest flow rate calculated for the coronary artery tree can be modified to reflect a hyperemia state instead of the rest state. For example, in an exemplary implementation, the total rest flow rate of the coronary artery tree can be calculated as described above in steps 106-110 and then a resting microvascular resistance at the termination of each branch of the coronary artery tree can be calculated based the total rest flow rate and a mean arterial pressure (MAP) calculated based on a heart rate, a systolic blood pressure, and a diastolic blood pressure non-invasively measured for the patient. A hyperemic microvascular resistance at the termination of each of branch can then be calculated based on the resting microvascular resistance, and the hyperemic microvascular resistances can be used as boundary conditions for simulation of hyperemic blood flow and pressure in the coronary artery tree. Additional details regarding calculating the resting microvascular resistance, MAP, and hyperemic microvascular resistance are described in U.S. Patent Publication No. 2013/0246034, entitled "Method and System for Non-Invasive Functional Assessment of Coronary Artery Stenosis," and U.S. Patent Publication No. 2014/00058715, entitled "Method and System for Non-Invasive Functional Assessment of Coronary Artery Stenosis," which are incorporated herein in their entirety by reference. In another possible implementation, the total rest flow rate calculated for the coronary artery tree can be mapped directly to a total hyperemia flow rate using the method described in U.S. patent application Ser. No. 14/599,678, entitled "System and Method for Mapping Patient Data from One Physiological State to Another Physiological State," filed on Jan. 19, 2015, which is incorporated herein in its entirety by reference. The total hyperemia flow rate can then be used as an inlet boundary condition for simulation of hyperemic blood flow and pressure in the coronary artery tree.

It is to be understood that other hemodynamic metrics may be similarly calculated using blood flow simulations at rest, hyperemia, or other physiological states. In an alternative embodiment, hemodynamic metrics can be calculated directly from the flow rates estimated for the branches of the coronary artery tree without performing blood flow simulations.

According to an advantageous embodiment of the present invention, the total rest flow rate can be calculated independently for the left coronary artery (LCA) or the right coronary artery (RCA) without modeling both of the LCA and the RCA. Accordingly, an advantage of the method of FIG. 1 is that this method may be performed individually for one of the LCA or the RCA in order to determine an inlet boundary condition and perform a blood flow simulation in the LCA or RCA, and calculate one or more hemodynamic metrics for a stenosis in the LCA or RCA. For example, the method of FIG. 1 can be performed individually in one of the LCA or RCA to assess a target stenosis in the LCA or RCA, without performing any modeling of the other one of the LCA or RCA that does not contain the target stenosis.

As described above, the method of FIG. 1 estimates a total rest flow rate and computed blood flow in a coronary artery tree. This method can be similarly applied to other arterial vessel trees, such as for renal circulation and cerebral circulation, as well. In addition, the method of FIG. 1 can be similarly applied to estimate a total flow rate for an artery tree at other physiological states than the rest state (e.g., hyperemia), for example by changing the operator $f_1$ used to map the reference radius for each branch to a rest flow rate.

Figure 4:
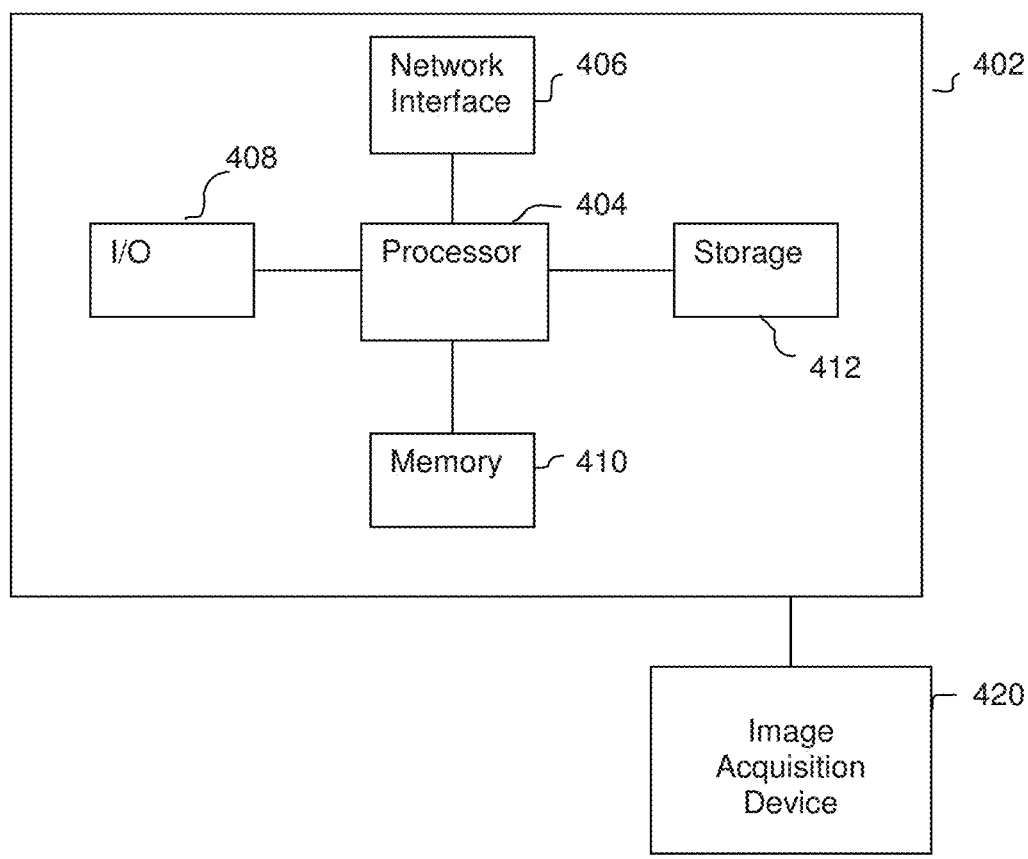
FIG. 4 is a high-level block diagram of a computer capable of implementing the present invention.

The above-described methods for computing blood flow in a coronary artery tree and non-invasive assessment of coronary artery stenosis may be implemented on a computer using well-known computer processors, memory units, storage devices, computer software, and other components. A high-level block diagram of such a computer is illustrated in FIG. 4. Computer 402 contains a processor 404, which controls the overall operation of the computer 402 by executing computer program instructions which define such operation. The computer program instructions may be stored in a storage device 412 (e.g., magnetic disk) and loaded into memory 410 when execution of the computer program instructions is desired. Thus, the steps of the method of FIG. 1 may be defined by the computer program instructions stored in the memory 410 and/or storage 412 and controlled by the processor 404 executing the computer program instructions. An image acquisition device 420, such as a CT scanning device, MR scanning device, Ultrasound device, etc., can be connected to the computer 402 to input image data to the computer 402. It is possible to implement the image acquisition device 420 and the computer 402 as one device. It is also possible that the image acquisition device 420 and the computer 402 communicate wirelessly through a network. In a possible embodiment, the computer 402 may be located remotely with respect to the image acquisition device 420 may perform the method steps as part of a server or cloud based service. The computer 402 also includes one or more network interfaces 406 for communicating with other devices via a network. The computer 402 also includes other input/output devices 408 that enable user interaction with the computer 402 (e.g., display, keyboard, mouse, speakers, buttons, etc.). Such input/output devices 408 may be used in conjunction with a set of computer programs as an annotation tool to annotate volumes received from the image acquisition device 420. One skilled in the art will recognize that an implementation of an actual computer could contain other components as well, and that FIG. 4 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for computing blood flow in coronary arteries from medical image data, comprising:
   extracting patient-specific anatomical measurements of a coronary artery tree from medical image data of a patient;
   estimating a reference radius for each of a plurality of branches in the coronary artery tree from the patient-specific anatomical measurements of the coronary artery tree;
   calculating a flow rate based on the reference radius for each of the plurality of branches of the coronary artery tree;
   calculating a plurality of total flow rate estimates for the coronary artery tree, wherein each of the plurality of total flow rate estimates is calculated from the flow rates of branches from a respective one of a plurality of generations of branches; and
   calculating a total flow rate of the coronary artery tree based on the plurality of total flow rate estimates.

2. The method of claim 1, wherein extracting patient-specific anatomical measurements of a coronary artery tree from medical image data of a patient comprises:
   generating a patient-specific anatomical model of the coronary tree from the medical image data of the patient.

3. The method of claim 1, wherein estimating a reference radius for each of a plurality of branches in the coronary artery tree from the patient-specific anatomical measurements of the coronary artery tree comprises:
   calculating, for each of the plurality of branches, an average value of healthy radiuses over a length of the branch.

4. The method of claim 1, wherein estimating a reference radius for each of a plurality of branches in the coronary artery tree from the patient-specific anatomical measurements of the coronary artery tree comprises:
   calculating, for each of the plurality of branches, an average value of healthy radiuses over a length of the branch, excluding a percentage of largest radius values and a percentage of smallest radius values of the branch.

5. The method of claim 1, wherein estimating a reference radius for each of a plurality of branches in the coronary artery tree from the patient-specific anatomical measurements of the coronary artery tree comprises:
   calculating, for each of the plurality of branches, a maximum or minimum value of healthy radiuses along a length of the branch.

6. The method of claim 1, wherein estimating a reference radius for each of a plurality of branches in the coronary artery tree from the patient-specific anatomical measurements of the coronary artery tree comprises:
   calculating the reference radius for at least one branch of the plurality of branches as a function of the reference radius values of a parent branch, one or more sibling branches, and one or more daughter branches.

7. The method of claim 1, wherein calculating a plurality of total flow rate estimates for the coronary artery tree, wherein each of the plurality of total flow rate estimates is calculated from the flow rates of branches from a respective one of a plurality of generations of branches comprises, for each of the plurality of generations of branches:
calculating an estimate for the total flow rate of the coronary artery tree as a function of the rest flow rates of all branches in that generation of branches and all terminal branches with a generation number smaller than that generation of branches.

8. The method of claim 7, wherein calculating an estimate for the total flow rate of the coronary artery tree as a function of the total flow rates of all branches in that generation of branches and all terminal branches with a generation number smaller than that generation of branches comprises:
assigning a weight to each of the branches in that generation of branches and the terminal branches with a generation number smaller than that generation branches;
calculating the estimate for the total rest flow rate of the coronary artery tree as a function of the rest flow rates of branches in that generation of branches and terminal branches with a generation number smaller than that generation branches and the weights assigned to each of the branches in that generation of branches and the terminal branches with a generation number smaller than that generation branches.

9. The method of claim 8, wherein assigning a weight to each of the branches in that generation of branches and the terminal branches with a generation number smaller than that generation branches comprises:
assigning the weights to each of the branches in that generation of branches and the terminal branches with a generation number smaller than that generation branches based on at least one of a length of the branch or a percentage of the branch that is diseased.

10. The method of claim 1, wherein calculating a total flow rate of the coronary artery tree based on the plurality of total flow rate estimates comprises:
calculating the total flow rate of the coronary artery tree as a function of the plurality of total flow rate estimates and weights corresponding to the plurality of generations of branches.

11. The method of claim 10, wherein calculating the total flow rate of the coronary artery tree as a function of the plurality of total flow rate estimates and weights corresponding the plurality of generations of branches comprises:
assigning a weight to each of the plurality of generations of branches based on a generation number of each generation of branches; and
calculating the total flow rate of the coronary artery tree as a function of the plurality of total flow rate estimates, each weighted by the weight assigned to the generation of branches from which that total flow rate estimate is calculated.

12. The method of claim 1, further comprising:
simulating blood flow and pressure in the coronary artery tree based on the patient-specific anatomical measurements of the coronary artery tree using the total flow rate of the coronary artery tree as an inlet boundary condition.

13. The method of claim 12, further comprising:
calculating at least one hemodynamic metric based on the simulated blood flow and pressure in the coronary artery tree.

14. The method of claim 1, wherein calculating a flow rate based on the reference radius for each of the plurality of branches of the coronary artery tree comprises:
calculating a rest flow rate based on the reference radius for each of the plurality of branches of the coronary artery tree, wherein the plurality of total flow rate estimates are a plurality of total rest flow rate estimates and the total flow rate calculated for the coronary artery tree is a total rest flow rate of the coronary artery tree.

15. The method of claim 14, wherein calculating a rest flow rate based on the reference radius for each of the plurality of branches of the coronary artery tree comprises:
calculating the rest flow rate for each of the plurality of branches as a function of the reference radius estimated for the branch and a power coefficient assigned to the branch.

16. The method of claim 14, further comprising:
simulating resting blood flow and pressure in the coronary artery tree based on the patient-specific anatomical measurements of the coronary artery tree using the total rest flow rate of the coronary artery tree as an inlet boundary condition.

17. The method of claim 14, further comprising:
determining a hyperemia boundary condition based on the total rest flow rate of the coronary artery tree;
simulating hyperemic blood flow and pressure in the coronary artery tree based on the patient-specific anatomical measurements of the coronary artery tree and the hyperemia boundary condition; and
calculating fractional flow reserve (FFR) for a stenosis in the coronary artery tree based on the simulated hyperemic blood flow and pressure.

18. The method of claim 1, wherein calculating a flow rate based on the reference radius for each of the plurality of branches of the coronary artery tree comprises:
calculating a hyperemia flow rate based on the reference radius for each of the plurality of branches of the coronary artery tree, wherein the plurality of total flow rate estimates are a plurality of total hyperemia flow rate estimates and the total flow rate calculated for the coronary artery tree is a total hyperemia flow rate of the coronary artery tree.

19. The method of claim 1, further comprising:
simulating hyperemic blood flow and pressure in the coronary artery tree based on the patient-specific anatomical measurements of the coronary artery tree using the total hyperemia flow rate of the coronary artery tree as an inlet boundary condition; and
calculating fractional flow reserve (FFR) for a stenosis in the coronary artery tree based on the simulated hyperemic blood flow and pressure.

20. The method of claim 1, wherein the coronary artery tree is a portion less than a full coronary artery tree of the patient.

21. The method of claim 1, the coronary artery tree is a coronary artery tree of only one of a left coronary artery (LCA) or a right coronary artery (RCA).

22. An apparatus for computing blood flow in coronary arteries from medical image data, comprising:
means for extracting patient-specific anatomical measurements of a coronary artery tree from medical image data of a patient;

means for estimating a reference radius for each of a plurality of branches in the coronary artery tree from the patient-specific anatomical measurements of the coronary artery tree;
means for calculating a flow rate based on the reference radius for each of the plurality of branches of the coronary artery tree;
means for calculating a plurality of total flow rate estimates for the coronary artery tree, wherein each of the plurality of total flow rate estimates is calculated from the flow rates of branches from a respective one of a plurality of generations of branches; and
means for calculating a total flow rate of the coronary artery tree based on the plurality of total flow rate estimates.

23. The apparatus of claim 22, wherein the means for extracting patient-specific anatomical measurements of a coronary artery tree from medical image data of a patient comprises:
means for generating a patient-specific anatomical model of the coronary tree from the medical image data of the patient.

24. The apparatus of claim 22, wherein the means for calculating a plurality of total flow rate estimates for the coronary artery tree, wherein each of the plurality of total flow rate estimates is calculated from the flow rates of branches from a respective one of a plurality of generations of branches comprises:
means for calculating, for each of the plurality of generations of branches, an estimate for the total flow rate of the coronary artery tree as a function of the rest flow rates of all branches in that generation of branches and all terminal branches with a generation number smaller than that generation of branches.

25. The apparatus of claim 22, wherein the means for calculating a total flow rate of the coronary artery tree based on the plurality of total flow rate estimates comprises:
means for calculating the total flow rate of the coronary artery tree as a function of the plurality of total flow rate estimates and weights corresponding the plurality of generations of branches.

26. The apparatus of claim 22, further comprising:
means for simulating blood flow and pressure in the coronary artery tree based on the patient-specific anatomical measurements of the coronary artery tree using the total flow rate of the coronary artery tree as an inlet boundary condition.

27. The apparatus of claim 26, further comprising:
means for calculating at least one hemodynamic metric based on the simulated blood flow and pressure in the coronary artery tree.

28. The apparatus of claim 22, wherein the means for calculating a flow rate based on the reference radius for each of the plurality of branches of the coronary artery tree comprises:
means for calculating a rest flow rate based on the reference radius for each of the plurality of branches of the coronary artery tree, wherein the plurality of total flow rate estimates are a plurality of total rest flow rate estimates and the total flow rate calculated for the coronary artery tree is a total rest flow rate of the coronary artery tree.

29. A non-transitory computer readable medium storing computer program instructions for computing blood flow in coronary arteries from medical image data, the computer program instructions when executed by a processor cause the processor to perform operations comprising:
extracting patient-specific anatomical measurements of a coronary artery tree from medical image data of a patient;
estimating a reference radius for each of a plurality of branches in the coronary artery tree from the patient-specific anatomical measurements of the coronary artery tree;
calculating a flow rate based on the reference radius for each of the plurality of branches of the coronary artery tree;
calculating a plurality of total flow rate estimates for the coronary artery tree, wherein each of the plurality of total flow rate estimates is calculated from the flow rates of branches from a respective one of a plurality of generations of branches; and
calculating a total flow rate of the coronary artery tree based on the plurality of total flow rate estimates.

30. The non-transitory computer readable medium of claim 29, wherein extracting patient-specific anatomical measurements of a coronary artery tree from medical image data of a patient comprises:
generating a patient-specific anatomical model of the coronary tree from the medical image data of the patient.

31. The non-transitory computer readable medium of claim 29, wherein estimating a reference radius for each of a plurality of branches in the coronary artery tree from the patient-specific anatomical measurements of the coronary artery tree comprises:
calculating, for each of the plurality of branches, an average value of healthy radiuses over a length of the branch.

32. The non-transitory computer readable medium of claim 29, wherein estimating a reference radius for each of a plurality of branches in the coronary artery tree from the patient-specific anatomical measurements of the coronary artery tree comprises:
calculating, for each of the plurality of branches, an average value of healthy radiuses over a length of the branch, excluding a percentage of largest radius values and a percentage of smallest radius values of the branch.

33. The non-transitory computer readable medium of claim 29, wherein estimating a reference radius for each of a plurality of branches in the coronary artery tree from the patient-specific anatomical measurements of the coronary artery tree comprises:
calculating, for each of the plurality of branches, a maximum or minimum value of healthy radiuses along a length of the branch.

34. The non-transitory computer readable medium of claim 29, wherein estimating a reference radius for each of a plurality of branches in the coronary artery tree from the patient-specific anatomical measurements of the coronary artery tree comprises:
calculating the reference radius for at least one branch of the plurality of branches as a function of the reference radius values of a parent branch, one or more sibling branches, and one or more daughter branches.

35. The non-transitory computer readable medium of claim 29, wherein calculating a plurality of total flow rate estimates for the coronary artery tree, wherein each of the plurality of total flow rate estimates is calculated from the flow rates of branches from a respective one of a plurality of generations of branches comprises, for each of the plurality of generations of branches:

calculating an estimate for the total flow rate of the coronary artery tree as a function of the rest flow rates of all branches in that generation of branches and all terminal branches with a generation number smaller than that generation of branches.

36. The non-transitory computer readable medium of claim 35, wherein calculating an estimate for the total flow rate of the coronary artery tree as a function of the total flow rates of all branches in that generation of branches and all terminal branches with a generation number smaller than that generation of branches comprises:
assigning a weight to each of the branches in that generation of branches and the terminal branches with a generation number smaller than that generation branches;
calculating the estimate for the total rest flow rate of the coronary artery tree as a function of the rest flow rates of branches in that generation of branches and terminal branches with a generation number smaller than that generation branches and the weights assigned to each of the branches in that generation of branches and the terminal branches with a generation number smaller than that generation branches.

37. The non-transitory computer readable medium of claim 36, wherein assigning a weight to each of the branches in that generation of branches and the terminal branches with a generation number smaller than that generation branches comprises:
assigning the weights to each of the branches in that generation of branches and the terminal branches with a generation number smaller than that generation branches based on at least one of a length of the branch or a percentage of the branch that is diseased.

38. The non-transitory computer readable medium of claim 29, wherein calculating a total flow rate of the coronary artery tree based on the plurality of total flow rate estimates comprises:
calculating the total flow rate of the coronary artery tree as a function of the plurality of total flow rate estimates and weights corresponding to the plurality of generations of branches.

39. The non-transitory computer readable medium of claim 38, wherein calculating the total flow rate of the coronary artery tree as a function of the plurality of total flow rate estimates and weights corresponding the plurality of generations of branches comprises:
assigning a weight to each of the plurality of generations of branches based on a generation number of each generation of branches; and
calculating the total flow rate of the coronary artery tree as a function of the plurality of total flow rate estimates, each weighted by the weight assigned to the generation of branches from which that total flow rate estimate is calculated.

40. The non-transitory computer readable medium of claim 29, wherein the operations further comprise:
simulating blood flow and pressure in the coronary artery tree based on the patient-specific anatomical measurements of the coronary artery tree using the total flow rate of the coronary artery tree as an inlet boundary condition.

41. The non-transitory computer readable medium of claim 40, wherein the operations further comprise:
calculating at least one hemodynamic metric based on the simulated blood flow and pressure in the coronary artery tree.

42. The non-transitory computer readable medium of claim 29, wherein calculating a flow rate based on the reference radius for each of the plurality of branches of the coronary artery tree comprises:
calculating a rest flow rate based on the reference radius for each of the plurality of branches of the coronary artery tree, wherein the plurality of total flow rate estimates are a plurality of total rest flow rate estimates and the total flow rate calculated for the coronary artery tree is a total rest flow rate of the coronary artery tree.

43. The non-transitory computer readable medium of claim 42, wherein calculating a rest flow rate based on the reference radius for each of the plurality of branches of the coronary artery tree comprises:
calculating the rest flow rate for each of the plurality of branches as a function of the reference radius estimated for the branch and a power coefficient assigned to the branch.

44. The non-transitory computer readable medium of claim 42, wherein the operations further comprise:
simulating resting blood flow and pressure in the coronary artery tree based on the patient-specific anatomical measurements of the coronary artery tree using the total rest flow rate of the coronary artery tree as an inlet boundary condition.

45. The non-transitory computer readable medium of claim 42, wherein the operations further comprise:
determining a hyperemia boundary condition based on the total rest flow rate of the coronary artery tree;
simulating hyperemic blood flow and pressure in the coronary artery tree based on the patient-specific anatomical measurements of the coronary artery tree and the hyperemia boundary condition; and
calculating fractional flow reserve (FFR) for a stenosis in the coronary artery tree based on the simulated hyperemic blood flow and pressure.

46. The non-transitory computer readable medium of claim 29, wherein calculating a flow rate based on the reference radius for each of the plurality of branches of the coronary artery tree comprises:
calculating a hyperemia flow rate based on the reference radius for each of the plurality of branches of the coronary artery tree, wherein the plurality of total flow rate estimates are a plurality of total hyperemia flow rate estimates and the total flow rate calculated for the coronary artery tree is a total hyperemia flow rate of the coronary artery tree.

47. The non-transitory computer readable medium of claim 46, wherein the operations further comprise:
simulating hyperemic blood flow and pressure in the coronary artery tree based on the patient-specific anatomical measurements of the coronary artery tree using the total hyperemia flow rate of the coronary artery tree as an inlet boundary condition; and
calculating fractional flow reserve (FFR) for a stenosis in the coronary artery tree based on the simulated hyperemic blood flow and pressure.

* * * * *